US009605284B2

(12) United States Patent
Lee et al.

(10) Patent No.: US 9,605,284 B2
(45) Date of Patent: Mar. 28, 2017

(54) **ACID-RESISTANCE IN *KLUYVEROMYCES MARXIANUS* BY ENGINEERING TRANSCRIPTIONAL FACTOR**

(71) Applicant: Samsung Electronics Co., Ltd., Suwon-si, Gyeonggi-do (KR)

(72) Inventors: Juyoung Lee, Daegu (KR); Hyunmin Koo, Seoul (KR); Jaechan Park, Yongin-si (KR); Jieun Kim, Suwon-si (KR); Jinha Kim, Namyangju-si (KR); Joonsong Park, Seoul (KR); Soonchun Chung, Seoul (KR); Byungkwan Cho, Daejeon (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 86 days.

(21) Appl. No.: 14/531,508

(22) Filed: Nov. 3, 2014

(65) Prior Publication Data

US 2015/0125918 A1 May 7, 2015

(30) Foreign Application Priority Data

Nov. 1, 2013 (KR) ........................ 10-2013-0132526

(51) Int. Cl.

| | |
|---|---|
| ***C12P 7/42*** | (2006.01) |
| ***C07K 14/39*** | (2006.01) |
| ***C07K 14/47*** | (2006.01) |
| ***C12N 9/12*** | (2006.01) |
| *C12P 7/18* | (2006.01) |
| *C12P 7/46* | (2006.01) |
| *C12P 7/56* | (2006.01) |

(52) U.S. Cl.
CPC ................ *C12P 7/42* (2013.01); *C07K 14/39* (2013.01); *C07K 14/4705* (2013.01); *C12N 9/1247* (2013.01); *C12P 7/18* (2013.01); *C12P 7/46* (2013.01); *C12P 7/56* (2013.01); *Y02P 20/52* (2015.11)

(58) Field of Classification Search
None
See application file for complete search history.

(56) References Cited

U.S. PATENT DOCUMENTS

2010/0210017 A1 8/2010 Gill et al.

FOREIGN PATENT DOCUMENTS

| | | | |
|---|---|---|---|
| KR | 2012-0029782 | A | 3/2012 |
| WO | WO 2009/116286 | A1 | 9/2009 |
| WO | WO 2010/011874 | A2 | 1/2010 |
| WO | WO 2011/099243 | A1 | 8/2011 |
| WO | WO 2011/114613 | A1 | 9/2011 |

OTHER PUBLICATIONS

Ngo et al. In the Protein Folding Problem and Tertiary Structure Prediction, 1994, Merz et al. (ed.), Birkhauser, Boston, MA, pp. 433 and 492-495.*

Warnecke et al., "A genomics approach to improve the analysis and design of strain selections," *Metabolic Engineering*, 10: 154-165 (2008).

Warnecke et al., "Rapid dissection of a complex phenotype through genomic-scale mapping of fitness altering genes," *Metabolic Engineering*,12: 241-250 (2010).

* cited by examiner

*Primary Examiner* — Richard Hutson
(74) *Attorney, Agent, or Firm* — Leydig, Voit & Mayer, Ltd.

(57) ABSTRACT

A microorganism with improved acid-resistance. A microorganism capable of efficiently producing 3-HP, and methods for producing an organic acid.

17 Claims, 2 Drawing Sheets

SEQUENCE LISTING

```
<160> NUMBER OF SEQ ID NOS: 14

<210> SEQ ID NO 1
<211> LENGTH: 233
<212> TYPE: PRT
<213> ORGANISM: Artificial Sequence
<220> FEATURE:
<223> OTHER INFORMATION: Synthetic (TBP15 (wild-type amino acids
      sequence))

<400> SEQUENCE: 1

Met Ser Glu Asp Asp Arg Met Lys Gln Phe Gln Gln Glu Asn Lys Ile
1               5                   10                  15

Val Phe Asp Pro Ser Thr Arg Ser Val Trp Glu Ser Gln Glu Lys Arg
            20                  25                  30

Glu His Glu Ser Leu Pro Gly Thr Asp Ala Asn Gly Asp Glu Gly Glu
        35                  40                  45

Lys Gly Ser Ala Thr Ser Gly Ile Ile Pro Thr Leu Gln Asn Ile Val
```

```
    50                  55                  60

Ala Thr Val Asn Leu Asp Cys Arg Leu Asp Leu Lys Thr Val Ala Leu
65                  70                  75                  80

His Ala Arg Asn Ala Glu Tyr Asn Pro Lys Arg Phe Ala Ala Val Ile
                85                  90                  95

Met Arg Ile Arg Glu Pro Lys Thr Thr Ala Leu Ile Phe Ala Ser Gly
            100                 105                 110

Lys Met Val Val Thr Gly Ala Lys Ser Glu Asp Asp Ser Lys Leu Ala
        115                 120                 125

Ser Arg Lys Tyr Ala Arg Ile Ile Gln Lys Ile Gly Phe Ser Ala Lys
    130                 135                 140

Phe Thr Asp Phe Lys Ile Gln Asn Ile Val Gly Ser Cys Asp Val Lys
145                 150                 155                 160

Phe Pro Ile Arg Leu Glu Gly Leu Ala Phe Ser His Gly Thr Phe Ser
                165                 170                 175

Ser Tyr Glu Pro Glu Leu Phe Pro Gly Leu Ile Tyr Arg Met Val Lys
            180                 185                 190

Pro Lys Ile Val Leu Leu Ile Phe Val Ser Gly Lys Ile Val Leu Thr
        195                 200                 205

Gly Ala Lys Gln Arg Glu Glu Ile Tyr Gln Ala Phe Glu Ala Ile Tyr
    210                 215                 220

Pro Val Leu Ser Glu Phe Arg Lys Leu
225                 230


<210> SEQ ID NO 2
<211> LENGTH: 233
<212> TYPE: PRT
<213> ORGANISM: Artificial Sequence
<220> FEATURE:
<223> OTHER INFORMATION: Synthetic (TBP15-M1 (Mutated amini acids
      sequence))

<400> SEQUENCE: 2

Met Ser Glu Asp Asp Arg Met Lys Gln Phe Leu Gln Glu Asn Lys Ile
1               5                   10                  15

Val Phe Asp Pro Ser Thr Arg Ser Val Trp Gly Ser Gln Glu Lys Arg
            20                  25                  30

Glu His Glu Ser Leu Gln Gly Thr Asp Ala Asn Ala Asp Glu Gly Glu
        35                  40                  45

Lys Gly Ser Ala Thr Ser Gly Ile Ile Pro Thr Leu Gln Asn Ile Val
    50                  55                  60

Ala Thr Val Asn Leu Asp Cys Arg Leu Asp Leu Lys Thr Val Ala Leu
65                  70                  75                  80

His Ala Arg Asn Ala Glu Tyr Asn Pro Glu Arg Phe Ala Ala Val Ile
                85                  90                  95

Met Arg Ile Arg Glu Pro Lys Thr Thr Ala Leu Ile Phe Ala Ser Gly
            100                 105                 110

Lys Met Val Val Thr Gly Ala Lys Ser Glu Asp Asp Ser Lys Leu Ala
        115                 120                 125

Ser Arg Lys Tyr Ala Arg Ile Ile Gln Lys Ile Gly Phe Ser Ala Lys
    130                 135                 140

Phe Thr Asp Phe Lys Ile Gln Asn Ile Val Gly Ser Cys Asp Val Lys
145                 150                 155                 160

Phe Pro Ile Arg Leu Glu Gly Leu Ala Phe Ser His Gly Thr Phe Ser
                165                 170                 175
```

```
Ser Tyr Glu Pro Glu Leu Phe Pro Gly Leu Ile Tyr Arg Met Val Lys
            180                 185                 190

Pro Lys Ile Val Leu Leu Ile Phe Val Ser Gly Lys Thr Val Leu Thr
        195                 200                 205

Gly Ala Lys Gln Arg Glu Glu Ile His Gln Ala Phe Glu Ala Ile Tyr
    210                 215                 220

Pro Val Leu Ser Glu Phe Arg Lys Leu
225                 230


<210> SEQ ID NO 3
<211> LENGTH: 233
<212> TYPE: PRT
<213> ORGANISM: Artificial Sequence
<220> FEATURE:
<223> OTHER INFORMATION: Synthetic (TBP15-M2 (Mutated amini acids
      sequence))

<400> SEQUENCE: 3

Met Ser Glu Asp Asp Arg Met Lys Gln Phe Gln Gln Glu Asn Lys Ile
1               5                   10                  15

Val Phe Asp Pro Ser Thr Arg Ser Val Trp Glu Gly Gln Glu Arg Arg
            20                  25                  30

Glu His Glu Ser Leu Pro Gly Thr Asp Ala Asn Ala Asp Glu Gly Glu
        35                  40                  45

Lys Gly Ser Ala Thr Ser Gly Ile Ile Pro Thr Leu Gln Asn Ile Val
    50                  55                  60

Ala Thr Val Asn Leu Asp Cys Arg Leu Asp Leu Lys Thr Val Ala Leu
65                  70                  75                  80

His Ala Arg Asn Ser Glu Tyr Asn Pro Lys Arg Phe Ala Ala Val Ile
                85                  90                  95

Met Arg Ile Ser Glu Pro Lys Thr Thr Ala Leu Ile Phe Ala Ser Gly
            100                 105                 110

Lys Met Val Val Thr Gly Ala Lys Ser Glu Asp Asp Ser Lys Leu Ala
        115                 120                 125

Cys Arg Lys Tyr Ala Arg Ile Ile Gln Lys Ile Gly Phe Ser Ala Lys
    130                 135                 140

Phe Thr Asp Phe Lys Ile Gln Asp Ile Val Gly Ser Cys Asp Val Lys
145                 150                 155                 160

Phe Pro Ile Arg Leu Glu Gly Leu Ala Phe Ser His Gly Thr Phe Ser
                165                 170                 175

Ser Cys Glu Pro Glu Leu Phe Pro Gly Leu Ile Tyr Arg Met Val Lys
            180                 185                 190

Pro Lys Ile Val Leu Leu Ile Phe Asp Ser Gly Lys Ile Val Leu Thr
        195                 200                 205

Gly Ala Lys Gln Arg Glu Glu Ile Tyr Gln Ala Phe Glu Ala Ile Tyr
    210                 215                 220

Pro Val Leu Ser Glu Phe Arg Lys Leu
225                 230


<210> SEQ ID NO 4
<211> LENGTH: 233
<212> TYPE: PRT
<213> ORGANISM: Artificial Sequence
<220> FEATURE:
<223> OTHER INFORMATION: Synthetic (TBP15-M3 (Mutated amini acids
      sequence))

<400> SEQUENCE: 4
```

```
Met Ser Glu Asp Asp Arg Met Lys Gln Phe Gln Gln Glu Asn Lys Ile
1               5                   10                  15

Val Phe Asp Pro Ser Thr Arg Ser Val Trp Glu Ser Gln Glu Lys Arg
            20                  25                  30

Glu His Glu Ser Leu Pro Gly Thr Asp Ala Asn Ala Asp Glu Gly Glu
        35                  40                  45

Lys Gly Ser Ala Thr Ser Gly Ile Ile Pro Thr Leu Gln Asn Ile Val
    50                  55                  60

Ala Thr Val Asn Leu Asp Cys Arg Leu Asp Leu Lys Thr Val Ala Leu
65                  70                  75                  80

His Ala Arg Asn Ala Glu Tyr Asn Pro Lys Arg Phe Ala Ala Val Val
                85                  90                  95

Met Arg Ile Arg Glu Pro Lys Thr Thr Ala Leu Ile Phe Ala Ser Gly
            100                 105                 110

Lys Met Val Val Thr Gly Ala Lys Ser Glu Asp Asp Ser Glu Leu Ala
        115                 120                 125

Ser Arg Lys Tyr Ala Arg Ile Ile Gln Lys Ile Gly Phe Ser Ala Lys
    130                 135                 140

Phe Thr Asp Phe Lys Ile Gln Asn Ile Val Gly Ser Cys Asp Val Lys
145                 150                 155                 160

Phe Pro Ile Arg Leu Glu Gly Leu Ala Phe Ser His Gly Thr Phe Ser
                165                 170                 175

Ser Tyr Glu Pro Glu Leu Ile Pro Gly Leu Ile Tyr Arg Met Val Lys
            180                 185                 190

Pro Lys Ile Val Leu Leu Ile Phe Val Ser Gly Lys Ile Val Leu Thr
        195                 200                 205

Glu Ala Lys Gln Arg Glu Glu Ile Tyr Gln Ala Phe Glu Ala Ile Tyr
    210                 215                 220

Pro Val Leu Cys Glu Phe Arg Lys Leu
225                 230
```

<210> SEQ ID NO 5
<211> LENGTH: 1220
<212> TYPE: PRT
<213> ORGANISM: Chloroflexus aurantiacus

<400> SEQUENCE: 5

```
Met Ser Gly Thr Gly Arg Leu Ala Gly Lys Ile Ala Leu Ile Thr Gly
1               5                   10                  15

Gly Ala Gly Asn Ile Gly Ser Glu Leu Thr Arg Arg Phe Leu Ala Glu
            20                  25                  30

Gly Ala Thr Val Ile Ile Ser Gly Arg Asn Arg Ala Lys Leu Thr Ala
        35                  40                  45

Leu Ala Glu Arg Met Gln Ala Glu Ala Gly Val Pro Ala Lys Arg Ile
    50                  55                  60

Asp Leu Glu Val Met Asp Gly Ser Asp Pro Val Ala Val Arg Ala Gly
65                  70                  75                  80

Ile Glu Ala Ile Val Ala Arg His Gly Gln Ile Asp Ile Leu Val Asn
                85                  90                  95

Asn Ala Gly Ser Ala Gly Ala Gln Arg Arg Leu Ala Glu Ile Pro Leu
            100                 105                 110

Thr Glu Ala Glu Leu Gly Pro Gly Ala Glu Glu Thr Leu His Ala Ser
        115                 120                 125

Ile Ala Asn Leu Leu Gly Met Gly Trp His Leu Met Arg Ile Ala Ala
    130                 135                 140
```

-continued

```
Pro His Met Pro Val Gly Ser Ala Val Ile Asn Val Ser Thr Ile Phe
145                 150                 155                 160

Ser Arg Ala Glu Tyr Tyr Gly Arg Ile Pro Tyr Val Thr Pro Lys Ala
                165                 170                 175

Ala Leu Asn Ala Leu Ser Gln Leu Ala Ala Arg Glu Leu Gly Ala Arg
            180                 185                 190

Gly Ile Arg Val Asn Thr Ile Phe Pro Gly Pro Ile Glu Ser Asp Arg
        195                 200                 205

Ile Arg Thr Val Phe Gln Arg Met Asp Gln Leu Lys Gly Arg Pro Glu
    210                 215                 220

Gly Asp Thr Ala His His Phe Leu Asn Thr Met Arg Leu Cys Arg Ala
225                 230                 235                 240

Asn Asp Gln Gly Ala Leu Glu Arg Arg Phe Pro Ser Val Gly Asp Val
                245                 250                 255

Ala Asp Ala Ala Val Phe Leu Ala Ser Ala Glu Ser Ala Ala Leu Ser
            260                 265                 270

Gly Glu Thr Ile Glu Val Thr His Gly Met Glu Leu Pro Ala Cys Ser
        275                 280                 285

Glu Thr Ser Leu Leu Ala Arg Thr Asp Leu Arg Thr Ile Asp Ala Ser
    290                 295                 300

Gly Arg Thr Thr Leu Ile Cys Ala Gly Asp Gln Ile Glu Glu Val Met
305                 310                 315                 320

Ala Leu Thr Gly Met Leu Arg Thr Cys Gly Ser Glu Val Ile Ile Gly
                325                 330                 335

Phe Arg Ser Ala Ala Ala Leu Ala Gln Phe Glu Gln Ala Val Asn Glu
            340                 345                 350

Ser Arg Arg Leu Ala Gly Ala Asp Phe Thr Pro Pro Ile Ala Leu Pro
        355                 360                 365

Leu Asp Pro Arg Asp Pro Ala Thr Ile Asp Ala Val Phe Asp Trp Gly
    370                 375                 380

Ala Gly Glu Asn Thr Gly Gly Ile His Ala Ala Val Ile Leu Pro Ala
385                 390                 395                 400

Thr Ser His Glu Pro Ala Pro Cys Val Ile Glu Val Asp Asp Glu Arg
                405                 410                 415

Val Leu Asn Phe Leu Ala Asp Glu Ile Thr Gly Thr Ile Val Ile Ala
            420                 425                 430

Ser Arg Leu Ala Arg Tyr Trp Gln Ser Gln Arg Leu Thr Pro Gly Ala
        435                 440                 445

Arg Ala Arg Gly Pro Arg Val Ile Phe Leu Ser Asn Gly Ala Asp Gln
    450                 455                 460

Asn Gly Asn Val Tyr Gly Arg Ile Gln Ser Ala Ala Ile Gly Gln Leu
465                 470                 475                 480

Ile Arg Val Trp Arg His Glu Ala Glu Leu Asp Tyr Gln Arg Ala Ser
                485                 490                 495

Ala Ala Gly Asp His Val Leu Pro Pro Val Trp Ala Asn Gln Ile Val
            500                 505                 510

Arg Phe Ala Asn Arg Ser Leu Glu Gly Leu Glu Phe Ala Cys Ala Trp
        515                 520                 525

Thr Ala Gln Leu Leu His Ser Gln Arg His Ile Asn Glu Ile Thr Leu
    530                 535                 540

Asn Ile Pro Ala Asn Ile Ser Ala Thr Thr Gly Ala Arg Ser Ala Ser
545                 550                 555                 560
```

```
Val Gly Trp Ala Glu Ser Leu Ile Gly Leu His Leu Gly Lys Val Ala
                565                 570                 575

Leu Ile Thr Gly Gly Ser Ala Gly Ile Gly Gly Gln Ile Gly Arg Leu
            580                 585                 590

Leu Ala Leu Ser Gly Ala Arg Val Met Leu Ala Ala Arg Asp Arg His
        595                 600                 605

Lys Leu Glu Gln Met Gln Ala Met Ile Gln Ser Glu Leu Ala Glu Val
    610                 615                 620

Gly Tyr Thr Asp Val Glu Asp Arg Val His Ile Ala Pro Gly Cys Asp
625                 630                 635                 640

Val Ser Ser Glu Ala Gln Leu Ala Asp Leu Val Glu Arg Thr Leu Ser
                645                 650                 655

Ala Phe Gly Thr Val Asp Tyr Leu Ile Asn Asn Ala Gly Ile Ala Gly
            660                 665                 670

Val Glu Glu Met Val Ile Asp Met Pro Val Glu Gly Trp Arg His Thr
        675                 680                 685

Leu Phe Ala Asn Leu Ile Ser Asn Tyr Ser Leu Met Arg Lys Leu Ala
    690                 695                 700

Pro Leu Met Lys Lys Gln Gly Ser Gly Tyr Ile Leu Asn Val Ser Ser
705                 710                 715                 720

Tyr Phe Gly Gly Glu Lys Asp Ala Ala Ile Pro Tyr Pro Asn Arg Ala
                725                 730                 735

Asp Tyr Ala Val Ser Lys Ala Gly Gln Arg Ala Met Ala Glu Val Phe
            740                 745                 750

Ala Arg Phe Leu Gly Pro Glu Ile Gln Ile Asn Ala Ile Ala Pro Gly
        755                 760                 765

Pro Val Glu Gly Asp Arg Leu Arg Gly Thr Gly Glu Arg Pro Gly Leu
    770                 775                 780

Phe Ala Arg Arg Ala Arg Leu Ile Leu Glu Asn Lys Arg Leu Asn Glu
785                 790                 795                 800

Leu His Ala Ala Leu Ile Ala Ala Ala Arg Thr Asp Glu Arg Ser Met
                805                 810                 815

His Glu Leu Val Glu Leu Leu Leu Pro Asn Asp Val Ala Ala Leu Glu
            820                 825                 830

Gln Asn Pro Ala Ala Pro Thr Ala Leu Arg Glu Leu Ala Arg Arg Phe
        835                 840                 845

Arg Ser Glu Gly Asp Pro Ala Ala Ser Ser Ser Ser Ala Leu Leu Asn
    850                 855                 860

Arg Ser Ile Ala Ala Lys Leu Leu Ala Arg Leu His Asn Gly Gly Tyr
865                 870                 875                 880

Val Leu Pro Ala Asp Ile Phe Ala Asn Leu Pro Asn Pro Pro Asp Pro
                885                 890                 895

Phe Phe Thr Arg Ala Gln Ile Asp Arg Glu Ala Arg Lys Val Arg Asp
            900                 905                 910

Gly Ile Met Gly Met Leu Tyr Leu Gln Arg Met Pro Thr Glu Phe Asp
        915                 920                 925

Val Ala Met Ala Thr Val Tyr Tyr Leu Ala Asp Arg Asn Val Ser Gly
    930                 935                 940

Glu Thr Phe His Pro Ser Gly Gly Leu Arg Tyr Glu Arg Thr Pro Thr
945                 950                 955                 960

Gly Gly Glu Leu Phe Gly Leu Pro Ser Pro Glu Arg Leu Ala Glu Leu

                965                 970                 975

Val Gly Ser Thr Val Tyr Leu Ile Gly Glu His Leu Thr Glu His Leu
```

```
            980                 985                 990

Asn Leu Leu Ala Arg Ala Tyr Leu  Glu Arg Tyr Gly Ala  Arg Gln Val
        995                 1000                1005

Val Met  Ile Val Glu Thr Glu  Thr Gly Ala Glu Thr  Met Arg Arg
    1010                 1015                1020

Leu Leu  His Asp His Val Glu  Ala Gly Arg Leu Met  Thr Ile Val
    1025                 1030                1035

Ala Gly  Asp Gln Ile Glu Ala  Ala Ile Asp Gln Ala  Ile Thr Arg
    1040                 1045                1050

Tyr Gly  Arg Pro Gly Pro Val  Val Cys Thr Pro Phe  Arg Pro Leu
    1055                 1060                1065

Pro Thr  Val Pro Leu Val Gly  Arg Lys Asp Ser Asp  Trp Ser Thr
    1070                 1075                1080

Val Leu  Ser Glu Ala Glu Phe  Ala Glu Leu Cys Glu  His Gln Leu
    1085                 1090                1095

Thr His  His Phe Arg Val Ala  Arg Lys Ile Ala Leu  Ser Asp Gly
    1100                 1105                1110

Ala Ser  Leu Ala Leu Val Thr  Pro Glu Thr Thr Ala  Thr Ser Thr
    1115                 1120                1125

Thr Glu  Gln Phe Ala Leu Ala  Asn Phe Ile Lys Thr  Thr Leu His
    1130                 1135                1140

Ala Phe  Thr Ala Thr Ile Gly  Val Glu Ser Glu Arg  Thr Ala Gln
    1145                 1150                1155

Arg Ile  Leu Ile Asn Gln Val  Asp Leu Thr Arg Arg  Ala Arg Ala
    1160                 1165                1170

Glu Glu  Pro Arg Asp Pro His  Glu Arg Gln Gln Glu  Leu Glu Arg
    1175                 1180                1185

Phe Ile  Glu Ala Val Leu Leu  Val Thr Ala Pro Leu  Pro Pro Glu
    1190                 1195                1200

Ala Asp  Thr Arg Tyr Ala Gly  Arg Ile His Arg Gly  Arg Ala Ile
    1205                 1210                1215

Thr Val
    1220


<210> SEQ ID NO 6
<211> LENGTH: 263
<212> TYPE: PRT
<213> ORGANISM: Escherichia coli

<400> SEQUENCE: 6

Met Arg Asn Ser Glu Met Ile Val Leu Val Thr Gly Ala Thr Ala Gly
1               5                   10                  15

Phe Gly Glu Ser Ile Thr Arg Arg Phe Ile Gln Gln Gly Asn Lys Val
            20                  25                  30

Ile Ala Thr Gly Arg Arg Gln Glu Arg Gly Gly Gly Trp Lys Lys Lys
        35                  40                  45

Lys Glu Arg Leu Gln Glu Leu Lys Asp Glu Leu Gly Asp Asn Leu Tyr
    50                  55                  60

Ile Ala Gln Leu Asp Val Arg Asn Arg Ala Ala Ile Glu Glu Met Leu
65                  70                  75                  80

Ala Ser Leu Pro Ala Glu Trp Ser Asn Ile Asp Ile Leu Val Asn Asn
                85                  90                  95

Ala Gly Leu Ala Leu Gly Met Glu Pro Ala His Lys Ala Ser Val Glu
            100                 105                 110
```

```
Asp Trp Glu Thr Met Ile Asp Thr Asn Asn Lys Gly Leu Val Tyr Met
        115                 120                 125

Thr Arg Ala Val Leu Pro Gly Met Val Glu Arg Asn His Gly His Ile
    130                 135                 140

Ile Asn Ile Gly Ser Thr Ala Gly Ser Trp Pro Tyr Ala Gly Gly Asn
145                 150                 155                 160

Val Tyr Gly Ala Thr Lys Ala Phe Val Arg Gln Phe Ser Leu Asn Leu
                165                 170                 175

Arg Thr Asp Leu His Gly Thr Ala Val Arg Val Thr Asp Ile Glu Pro
            180                 185                 190

Gly Leu Val Gly Gly Thr Glu Phe Ser Asn Val Arg Phe Lys Gly Asp
        195                 200                 205

Asp Gly Lys Ala Glu Lys Thr Tyr Gln Asn Thr Val Ala Leu Thr Pro
    210                 215                 220

Glu Asp Val Ser Glu Ala Val Trp Trp Val Ser Thr Leu Pro Ala His
225                 230                 235                 240

Val Asn Ile Asn Thr Leu Glu Met Met Pro Val Thr Gln Ser Tyr Ala
                245                 250                 255

Gly Leu Asn Val His Arg Gln
            260


<210> SEQ ID NO 7
<211> LENGTH: 28
<212> TYPE: DNA
<213> ORGANISM: Artificial Sequence
<220> FEATURE:
<223> OTHER INFORMATION: Synthetic (TBP D1 F)

<400> SEQUENCE: 7

gctctagaat gtctgaagat gatagaat                                         28


<210> SEQ ID NO 8
<211> LENGTH: 20
<212> TYPE: DNA
<213> ORGANISM: Artificial Sequence
<220> FEATURE:
<223> OTHER INFORMATION: Synthetic (TBP D1 R)

<400> SEQUENCE: 8

taggtatgat tcccgatgta                                                  20


<210> SEQ ID NO 9
<211> LENGTH: 40
<212> TYPE: DNA
<213> ORGANISM: Artificial Sequence
<220> FEATURE:
<223> OTHER INFORMATION: Synthetic (TBP D2 F)

<400> SEQUENCE: 9

tacatcggga atcataccta ctctacagaa tattgttgcg                            40


<210> SEQ ID NO 10
<211> LENGTH: 20
<212> TYPE: DNA
<213> ORGANISM: Artificial Sequence
<220> FEATURE:
<223> OTHER INFORMATION: Synthetic (TBP D2 R)

<400> SEQUENCE: 10

gtaacaacca tcttaccaga                                                  20
```

-continued

```
<210> SEQ ID NO 11
<211> LENGTH: 40
<212> TYPE: DNA
<213> ORGANISM: Artificial Sequence
<220> FEATURE:
<223> OTHER INFORMATION: Synthetic (TBP D3 F)

<400> SEQUENCE: 11

tctggtaaga tggttgttac gggtgctaaa agtgaagatg                           40


<210> SEQ ID NO 12
<211> LENGTH: 20
<212> TYPE: DNA
<213> ORGANISM: Artificial Sequence
<220> FEATURE:
<223> OTHER INFORMATION: Synthetic (TBP D3 R)

<400> SEQUENCE: 12

gaaagtaccg tgactaaatg                                                 20


<210> SEQ ID NO 13
<211> LENGTH: 40
<212> TYPE: DNA
<213> ORGANISM: Artificial Sequence
<220> FEATURE:
<223> OTHER INFORMATION: Synthetic (TBP D4 F)

<400> SEQUENCE: 13

catttagtca cggtactttc tcgtcatatg aaccagaact                           40


<210> SEQ ID NO 14
<211> LENGTH: 29
<212> TYPE: DNA
<213> ORGANISM: Artificial Sequence
<220> FEATURE:
<223> OTHER INFORMATION: Synthetic (TBP D4 R)

<400> SEQUENCE: 14

tcccccgggt cattataatt ttctgaatt                                       29
```

ACID-RESISTANCE IN *KLUYVEROMYCES MARXIANUS* BY ENGINEERING TRANSCRIPTIONAL FACTOR

RELATED APPLICATIONS

This application claims the benefit of Korean Patent Application No. 10-2013-0132526, filed on Nov. 1, 2013, in the Korean Intellectual Property Office, the entire disclosure of which is hereby incorporated by reference.

INCORPORATION-BY-REFERENCE OF MATERIAL ELECTRONICALLY SUBMITTED

Incorporated by reference in its entirety herein is a computer-readable nucleotide/amino acid sequence listing submitted herewith and identified as follows: One 23,231 bytes ASCII (Text) file named "716913_ST25.TXT," created Oct. 30, 2014.

BACKGROUND

1. Field

The present disclosure relates to an improved acid-resistant *Kluyveromyces marxianus* and a strain that produces 3-hydroxypropionate with high efficiency prepared by using the same.

2. Description of the Related Art 3-hydroxypropionate (3-HP) is an organic acid. A calcium salt of 3-HP has a water solubility about one hundred times higher than that of a calcium salt of citric acid or malic acid and thus is useful in preventing scale in a boiler or an industrial facility. In addition, 3-HP is an important synthetic intermediate in several chemical processes. In particular, 3-HP is important in producing several chemicals and polymers including production of malonic acid by an oxidation reaction, production of a special-purpose polyester by an esterification with an alcohol, and production of 1,3-propanediol by a reduction reaction. In particular, 3-HP may be used as a precursor of acrylic acid, acrylic polymer, 1,3-propanediol, malonic acid, acrylamide, and others. For example, acrylic acid is used as a raw material for polymerization of a coating material, an adhesive, a detergent, and an absorbent. The market size of acrylic acid is about 8 trillion KRW in the world and about 140 billion KRW in Korea as of 2008.

Methods of preparing 3-HP may be classified as chemical methods and biological methods. Known chemical methods include a method of preparing 3-HP by using 1,3-propanediol as a starting material and palladium as a catalyst and a method of preparing 3-HP by using 3-hydroxypropionaldehyde in existence of palladium and platinum catalysts. In addition, a method of preparing 3-HP in which an ion exchange resin (Amberlyst 15) is used as a solid acid catalyst and a reaction is performed for 40 hours in a high pressure reactor by using acrylic acid as a starting material has been reported. The selectivity of this method of preparing 3-HP is 91% and the yield is 34%.

The biological method is to synthesize 3-HP by using a microorganism under high temperature and high pressure conditions. For example, reported biological methods of preparing 3-HP include a method of synthesizing 3-HP by using a *Candidarugosa* mutant (*Candidarugosa* KT8201) from acrylic acid, propionic acid, and propionaldehyde, a method of synthesizing 3-HP by using *Alcaligenes faecalis* M3A from acrylic acid, and a method of synthesizing 3-HP by using a *Escherichia coli* metabolic engineering technology from glucose. However, when a microorganism is used, the 3-HP productivity is low. Such a low productivity is a problem in producing 3-HP by using a biological process. In particular, as 3-HP is an acid, after a microorganism produces 3-HP over a certain level, the pH becomes too low and the microorganism is unable to produce more 3-HP.

Therefore, studies have continuously been conducted to find an appropriate and optimal microorganism to resolve the problem. One embodiment of the present invention provides a newly developed microorganism which is capable of surviving a low pH and a method of effectively producing 3-HP by using the same.

SUMMARY

One aspect of the present invention provides an improved acid-resistant microorganism. Another aspect of the present invention provides a microorganism capable of efficiently producing an organic acid. Another aspect of the present invention provides a method of efficiently producing 3-HP by using the improved acid-resistant microorganism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
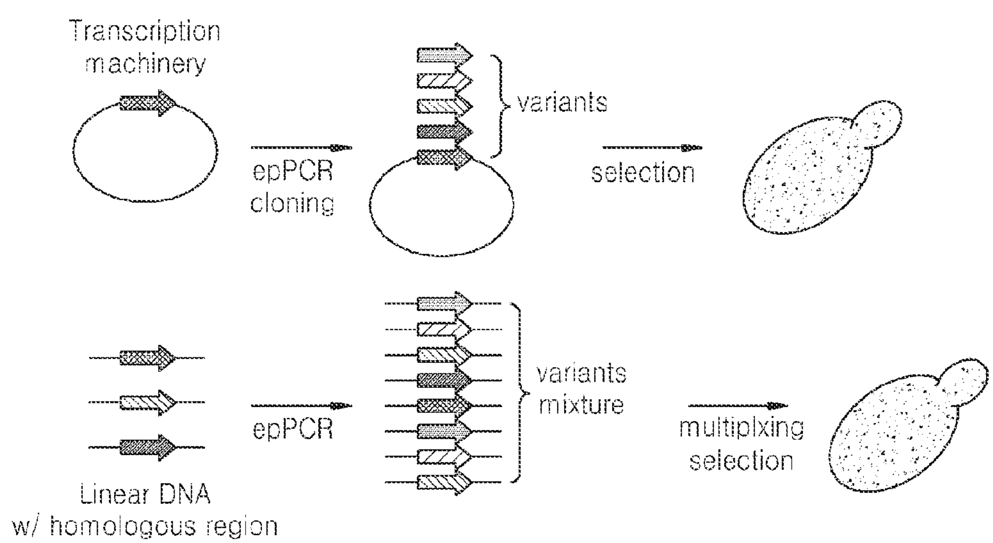
FIG. 1 is a schematic diagram depicting a method of modifying a phenotype of a strain by modifying genes related to a transcriptional machinery.
Figure 2:
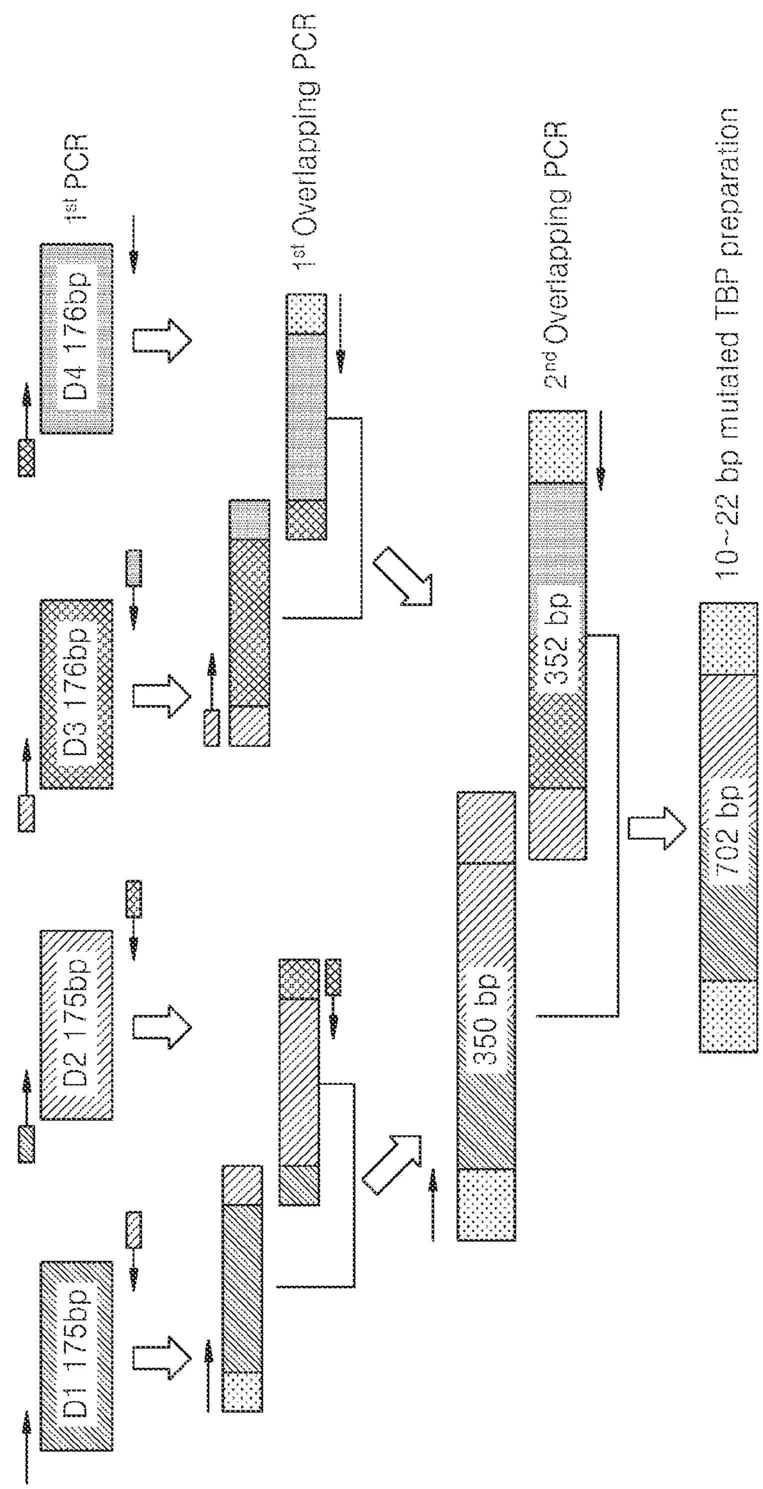
FIG. 2 is a diagram depicting a method of preparing a mutant library by performing an error-prone PCR with TBP among genes encoding transcription factors, in which the error-prone PCR was performed by dividing the full-length TBP gene (702 bp) into 175 bp domains or 176 bp domains.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Unless otherwise defined, all technical and scientific terms used herein have the same meaning as commonly understood by one of ordinary skill in the art to which this invention belongs. Generally, the nomenclature used herein is that well known and commonly employed in the art.

One aspect of the present invention provides a transformed (i.e., recombinant or genetically modified) microorganism with increased acid-resistance as compared to an unmodified (e.g., "wild-type") microorganism of the same type. The acid resistance is increased by genetic manipulation. One embodiment of the present invention provides a transformed microorganism in which a gene encoding a mutated polypeptide of the RNA polymerase II complex (i.e., the RNA polymerase II preinitiation complex) is expressed. The expression of the mutant RNA polymerase II complex is facilitated using a vector (e.g., expression vector) to express the gene encoding a mutant polypeptide sub-unit of the RNA polymerase II complex, or by inserting a gene encoding a mutant polypeptide sub-unit of the RNA polymerase II complex into a genome of the microorganism.

The term "RNA polymerase II complex" and "RNA polymerase II preinitiation complex" used herein refers to a protein complex having a function of copying a DNA to an RNA. The complex includes several subunit proteins. Specifically, the RNA polymerase II complex includes RNA polymerase II (RNAP II), transcription factor II D (TFIID), transcription factor II B (TFIIB), transcription factor II F (TFIIF), transcription factor II E (TFIIE), transcription factor II H (TFIIH), TATA-box binding protein (TBP), and TBP-associated factor (TAF).

The term "mutated RNA polymerase II complex" or "mutant RNA polymerase II complex" refers to an RNA polymerase II complex in which one of the subunit proteins included in the RNA polymerase II complex is modified or two or more of the subunit proteins are modified. The term "modification" or "modified" used herein refers to deletion or substitution of at least one of the amino acids included in a subunit protein, or addition of a new amino acid to a subunit protein. Such a modification may change the three-dimensional structure of a RNA polymerase II complex and thereby change the activity or function thereof. The modified RNA polymerase II complex may include a complex in which a gene encoding a subunit of the complex is modified. In addition, a subunit may be produced in a cell by the modified gene. Transcription of hypostasis genes (about 3,000 hypostasis genes) of which transcription is regulated by a protein produced by the modified gene is regulated and a change in protein expression is thereby induced. As a result, a microorganism including the modified gene may have a new phenotype and a new function which a general microorganism does not have. For example, the newly acquired phenotype may be an increased acid-resistance in a microorganism.

In addition, the microorganism may be *Kluyveromyces marxianus*. The increased acid-resistant *Kluyveromyces marxianus* is capable of surviving and growing at a pH of 5.0 or lower, even at a pH of 2.5 or lower.

The gene encoding the mutated RNA polymerase II complex subunit may be derived from any suitable organism, such as *Kluyveromyces marxianus* or *Saccharomyces cerevisiae*. For instance, the gene may be replaced by a gene having a DNA sequence and a corresponding amino acid sequence the same as or similar to those of the gene or a gene having the same or a similar function in a cell by searching genes of *Saccharomyces cerevisiae* in addition to *Kluyveromyces marxianus* and selecting one of the genes.

Modification of the gene may be accomplished by a known mutation method. The method includes deletion, insertion, and substitution of a gene. In addition, gene modification may be generated by an error-prone PCR (ep-PCR). An ep-PCR may be performed by a commonly known method. An ep-PCR may be performed by dividing a target gene into two or more domains. A domain may have 500 bp or less, or 400 bp or less. A domain may have 300 bp or less, 200 bp or less, or 100 bp or less. The number of domains and the size thereof may be appropriately chosen by one who is in the art according to the size of a gene. For example, the mutated RNA polymerase II complex may be caused by a mutated TBP. The mutated TBP may be a TBP including at least one mutated amino acid including amino acids of SEQ ID NOS: 2 to 4.

A polynucleotide encoding the mutated protein may be introduced to a strain without any modification or the polynucleotide may be inserted to a vector and then introduced to a strain. In addition, a transformed strain to which the polynucleotide is introduced may express a mutated protein.

The term "polynucleotide" used herein comprehensively refers to DNA (gDNA and cDNA) and RNA molecules. A nucleotide, which is the basic unit of a polynucleotide, includes not only a natural nucleotide but also an analogue in which a sugar or base part is modified.

The term "vector" used herein refers to a DNA product including a DNA sequence which is operably linked to an appropriate regulatory sequence capable of expressing the DNA in an appropriate strain. The vector may be a plasmid vector, a bacteriophage vector, or a cosmid vector. By expressing the vector, the gene may produce the modified protein. Or the gene may be inserted into a chromosome of a strain and expressed as part of the chromosome. In addition, the gene may be linked to an operable promoter.

For an expression vector to operate, an expression vector may include an origin of replication, a promoter, a multiple cloning site (MCS), a selectable marker, or a combination thereof. An origin of replication enables a plasmid to replicate independently of a chromosome of a host cell. A promoter functions in a transcription process of an introduced foreign gene. An MCS enables a foreign gene to be inserted through various restriction enzyme sites. A selectable marker verifies whether a vector has been properly introduced to a host cell or not. A selectable marker may include an antibiotic resistant gene. For example, there are antibiotic resistant genes which are resistant to ampicillin, gentamycin, carbenicillin, chloramphenicol, streptomycin, kanamycin, geneticin, neomycin, or tetracycline. Selection marker genes also encode proteins that confer resistance to antibiotics or other toxins such as zeocin (sh ble gene from *Streptoalloteichus hindustanus*), or G418 (kanamycin resistance gene), hygromycin (aminoglycoside antibiotic resistance). Also, the selection marker genes may encode proteins that complement auxotrophic deficiencies of the cell. For example, auxotrophic deficiencies are the amino acid leucine deficiency (e.g. LEU2 gene) or uracil deficiency (e.g. URA3 gene). Cells that are orotidine-5'-phosphate decarboxylase negative (ura3-) cannot grow on media lacking uracil. Thus a functional URA3 gene can be used as a marker on a cell having a uracil deficiency, and successful transformants can be selected on a medium lacking uracil. Only cells transformed with the functional URA3 gene are able to synthesize uracil and grow on such medium.

In addition, a promoter which may be used to express a protein may be a strong, constitutive promoter. The promoter may be a promoter selected from the group consisting of triose phosphate isomerase promoters, pyruvate decarboxylase promoter, alcohol dehydrogenase promoters and triose phosphate dehydrogenase promoter. Also, the promoter may include a promoter derived from a genome of a mammalian cell (e.g., metallothionein promoter) or a promoter derived from a mammalian virus (e.g., adenovirus late promoter, vaccinia virus 7.5 K promoter, SV40 promoter, cytomegalovirus promoter, and HSV tk promoter). The promoter may be a lamda PL promoter, a trp promoter, a lac promoter, or a T7 promoter. These promoters are operably linked to a sequence encoding a gene. The term "operably linked" used herein refers to a functional link between a nucleic acid expression regulation sequence (e.g., promoter, signal sequence, or an array at a transcription factor-binding site) and another nucleic acid sequence. By the linkage, the regulatory sequence regulates transcription and/or translation of a nucleic acid sequence encoding the gene.

The term "protein expression" used herein refers to existence of a protein or an enzyme having activity in a microorganism. In addition, the protein or enzyme may exist as a polynucleotide encoding a protein existing in a microorganism is transcribed from a polynucleotide to an mRNA which is then translated to a protein. A polynucleotide encoding a protein may be inserted to and exist in a chromosome of a microorganism or exist in a plasmid vector.

The term "transformation" herein refers to introducing a gene to a host cell so that the gene may be expressed in the microorganism. A transformed gene, only if the gene may be expressed in the host cell, may be any gene whether the gene is inserted into a chromosome of the host cell or the gene exists outside a chromosome. The gene, which is a polynucleotide capable of encoding a polypeptide, may be DNA or RNA. The introduction of the gene may be any type of introduction, only if the gene may be introduced into and expressed in the host cell. For example, the gene may be introduced into a host cell by an introduction in the form of an expression cassette, which is a polynucleotide structure including all factors related to the expression of the gene by itself. The expression cassette usually includes a promoter, a transcription termination signal, a ribosome binding site, and a translation termination signals operably linked to the gene. The expression cassette may be an expression vector capable of self-replication. In addition, the gene may be introduced as itself or in the form of a polynucleotide structure to a host cell and then be operably linked to a sequence related to an expression in the host cell.

Another aspect of the present invention provides a microorganism capable of efficiently producing an organic acid or a salt thereof by introducing a gene enabling to produce an organic acid into a microorganism of which acid-resistance is increased.

The organic acid may be a substance which is produced in the metabolic process of a microorganism. In addition to the polynucleotide encoding the mutated RNA polymerase II complex (e.g., gene encoding a mutant subunit), a microorganism may further include a polynucleotide encoding a polypeptide or enzyme involved in synthesis of an organic acid. For example, the organic acid may be lactic acid, succinic acid, malic acid, 3-HP, 4-hydroxybutyric acid, or 1,4-butandiol.

To synthesize lactic acid among the organic acids, a microorganism may further include lactate dehydrogenase. The lactate dehydrogenase enzyme catalyzes a reaction of converting pyruvate to lactate. The enzyme is also referred to as "Ldh." For example, the Ldh may be an enzyme classified as EC.1.1.1.27.

In addition, to produce 3-HP among the organic acids, various kinds of 3-HP production pathways may be introduced to a microorganism. A biological reaction pathway which does not exist in the microorganism, and may be introduced by way of genetic modification, may be at least one selected from the group consisting of malonyl CoA pathway, β-alanine pathway, and glycerol pathway.

The malonyl CoA pathway refers to production of malonyl-CoA from glucose. An enzyme catalyzing production of malonyl-CoA from glucose may be introduced to a microorganism and expressed in the microorganism. As an enzyme catalyzing the reaction, one or more of 3-hydroxyisobutryl-CoA hydrolase, 3-hydroxyisobutyrate dehydrogenase, 3-hydroxypropionyl-CoA hydrolase, 3-hydroxypropionyl-CoA dehydratase, acetyl-CoA carboxylase, aspartate decarboxylase, CoA transferase, malonyl-CoA reductase, phosphoenolpyruvate (PEP) carboxylase, 3-oxopropanoate: NADP+ oxidoreductase, malonate semialdehyde reductase, and 3-hydroxypropionate dehydrogenase may be used independently or a combination thereof may be used. In particular, 3-oxopropanoate:$NADP^+$ oxidoreductase and 3-hydroxypropionate dehydrogenase may be introduced.

The 3-hydroxyisobutryl-CoA hydrolase is an enzyme catalyzing a reaction of converting 3-hydroxy-2-methyl propanoyl-CoA to 3-hydroxy-2-methylpropanoate or the reverse reaction. In addition, the enzyme may be an enzyme classified as EC 3.1.2.4.

The 3-hydroxyisobutyrate dehydrogenase is an enzyme catalyzing a reaction of converting 3-hydroxy-2-methylpropanoate to 2-methyl-3-oxopropanoate or the reverse reaction. In addition, the enzyme may be an enzyme classified as EC 1.1.1.31.

The 3-hydroxypropionyl-CoA hydrolase is an enzyme catalyzing a reaction of converting 3-hydroxypropionyl-CoA to 3-hydroxypropionate or the reverse reaction. In addition, the enzyme may be an enzyme classified as EC 3.1.2.

The 3-hydroxypropionyl-CoA dehydratase is an enzyme catalyzing a reaction of converting 3-hydroxypropionyl-CoA to acryloyl-CoA or the reverse reaction. In addition, the enzyme may be an enzyme classified as EC 4.2.1.116.

The acetyl-CoA carboxylase is an enzyme catalyzing a reaction of converting acetyl-CoA to malonyl-CoA. In addition, the enzyme may be an enzyme classified as EC 6.4.1.2.

The aspartate decarboxylase is an enzyme catalyzing a reaction of converting L-aspartate to β-alanine or the reverse reaction. In addition, the enzyme may be an enzyme classified as EC 4.1.1.11.

The CoA transferase is an enzyme transferring CoA from acetyl-CoA to another substance. For example, the CoA transferase may be propionate CoA transferase, which is an enzyme catalyzing a reaction of producing propanoyl-CoA by transferring acetyl-CoA to propanoate. For example, the enzyme may be an enzyme classified as EC 2.8.3.1.

The malonyl-CoA reductase is an enzyme catalyzing a reaction of converting malonate semialdehyde to malonyl-CoA or the reverse reaction. In addition, the enzyme may be an enzyme classified as EC 1.2.1.75.

The PEP carboxylase is an enzyme catalyzing a reaction of converting phosphate and oxaloacetate to phosphoenolpyruvate or the reverse reaction. In addition, the enzyme may be an enzyme classified as EC 4.1.1.31.

The 3-oxopropanoate:$NADP^+$ oxidoreductase is an enzyme catalyzing a reaction of converting 3-oxopropanoate and CoA to acetyl-CoA or the reverse reaction. The enzyme is also referred to as malonate semialdehyde dehydrogenase. In addition, the enzyme may be an enzyme classified as EC 1.2.1.18.

The malonate semialdehyde reductase is an enzyme catalyzing a reaction of converting 3-hydroxypropionate to malonate semialdehyde or the reverse reaction. The enzyme may be an enzyme classified as EC 1.1.1.298.

The 3-hydroxypropionate dehydrogenase is an enzyme catalyzing a reaction of converting 3-hydroxypropanoate to 3-oxopropanoate or the reverse reaction. The enzyme may be an enzyme classified as EC 1.1.1.59.

In addition, a pathway may be introduced to catalyze a reaction of converting acetyl-coA to malonyl-coA, malonyl-coA to malonic semialdehyde, and malonic semialdehyde to 3-HP. To introduce the pathway, the malonyl-CoA reductase which catalyzes a reaction of converting malonyl-CoA to malonic semialdehyde and the malonate semialdehyde reductase which catalyzes a reaction of converting 3-HP to malonic semialdehyde may be introduced.

The purpose of introducing the β-alanine pathway into the microorganism is to introduce a pathway in which glucose passes through β-alanine. Although the β-alanine pathway has a neutral oxidation/reduction relationship, it is known that ATP may not be obtained from the β-alanine pathway. To introduce the β-alanine pathway, at least one of 3-hydroxyisobutyrate dehydrogenase, 4-aminobutyrate aminotransferase, acetyl-CoA carboxylase, aspartate aminotransferase, aspartate decarboxylase, glutamate dehydrogenase, OS17 enzyme, pyruvate carboxylase, β-alanyl-CoA ammonia lyase, and 3-hydroxypropionate dehydrogenase may be introduced. It may be appropriate to introduce 3-hydroxyisobutyrate dehydrogenase.

The 3-hydroxyisobutyrate dehydrogenase is an enzyme catalyzing a reaction of converting 3-hydroxy-2-methylpropanoate to 2-methyl-3-oxopropanoate or the reverse reaction. In addition, the enzyme may be an enzyme classified as EC 1.1.1.31.

The 4-aminobutyrate aminotransferase is an enzyme catalyzing a reaction of converting 4-aminobutanoate and 2-oxoglutarate to succinate semialdehyde and L-glutamate or the reverse reaction. In addition, the enzyme may be an enzyme classified as EC 2.6.1.19.

The acetyl-CoA carboxylase is an enzyme catalyzing a reaction of converting acetyl-CoA and $HCO_3$ to phosphate and malonyl-CoA or the reverse reaction. In addition, the enzyme may be an enzyme classified as EC 6.4.1.2.

The aspartate aminotransferase is an enzyme catalyzing a reaction of converting L-aspartate and 2-oxoglutarate to oxaloacetate and L-glutamate or the reverse reaction. In addition, the enzyme may be an enzyme classified as EC 2.6.1.1.

The aspartate decarboxylase is an enzyme catalyzing a reaction of converting L-aspartate to β-alanine or the reverse reaction. In addition, the enzyme may be an enzyme classified as EC 4.1.1.11.

The glutamate dehydrogenase is an enzyme catalyzing a reaction of converting L-glutamate and $NAD^+$ to oxoglutarate and NADH or the reverse reaction. In addition, the enzyme may be an enzyme classified as EC 1.4.1.2.

The OS17 enzyme is an enzyme catalyzing a reaction of converting propanoate and CoA to diphosphate and propanoyl-CoA or the reverse reaction. The enzyme is also called propionate-CoA ligase. In addition, the enzyme may be an enzyme classified as EC 6.2.1.17.

The pyruvate carboxylase is an enzyme catalyzing a reaction of converting pyruvate and $HCO_3$ to phosphate and oxaloacetate or the reverse reaction. In addition, the enzyme may be an enzyme classified as EC 6.4.1.1.

The β-alanyl-CoA ammonia lyase is an enzyme catalyzing a reaction of converting β-alanyl-CoA to acryloyl-CoA or the reverse reaction. In addition, the enzyme may be an enzyme classified as EC 4.3.1.6.

The 3-hydroxypropionate dehydrogenase is an enzyme catalyzing a reaction of converting 3-hydroxypropionate and $NAD^+$ to and 3-oxopropanoate and NADH or the reverse reaction. In addition, the enzyme may be an enzyme classified as EC 1.1.1.59.

The glycerol pathway using glucose as carbon source pass through 3-hydroxypropionaldehyde and is a direct linear pathway from a substrate to a product. To introduce the glycerol pathway, glycerol dehydratase and aldehyde dehydrogenase may be introduced.

The glycerol dehydratase is an enzyme catalyzing a reaction of converting glycerol to 3-hydroxypropanal or the reverse reaction. In addition, the enzyme may be an enzyme classified as EC 4.2.1.30.

The aldehyde dehydrogenase is an enzyme catalyzing a reaction of converting aldehyde and NAD to carboxylate and NADH or the reverse reaction. In addition, the enzyme may be an enzyme classified as EC 1.2.1.3.

Another aspect of the present invention provides a method of producing an organic acid by using the microorganism with improved acid-resistance, as described herein.

One embodiment of the present invention provides a method of producing an organic acid including culturing the microorganism of which acid-resistance is improved, and comprising a heterologous gene encoding a protein or enzyme involved in the production of an organic acid, in a cell culture medium, whereby the microorganism produces an organic acid, and recovering an organic acid from the culture solution. The organic acid may be, for example, lactic acid, succinic acid, malic acid, 3-HP, 4-hydroxybutyric acid, or 1,4-butandiol. In one embodiment of the present invention, the organic acid may be 3-HP.

The culturing may be performed under an appropriate culture medium and culture conditions known in this art. The culture medium and culture conditions may be conveniently adjusted according to the selected microorganism. The culturing method may include batch culturing, continuous culturing, fed-batch culturing or a combination thereof.

The microorganism may be *Kluyveromyces marxianus*.

The term "metabolite" refers to all substances produced by a metabolic reaction of a microorganism. The metabolite may be an intermediate product of a metabolic reaction of a microorganism or a final product of a metabolic reaction of a microorganism. Examples of metabolites are succinic acid, lactic acid, and 3-HP but not limited thereto.

The culture medium may include various carbon sources, nitrogen sources, and trace elements. The culture medium may be standard medium which is a complete medium for yeast growth. The culture medium may be yeast extract peptone dextrose (YPD) medium. The YPD medium may include yeast extract, peptone, double-distilled water, and glucose (or dextrose). The YPD medium may be used as solid medium by including agar. The yeast extract may include all the amino acids necessary for growth.

The carbon source may include a carbohydrate such as glucose, sucrose, lactose, fructose, maltose, starch, and cellulose, a lipid such as soybean oil, sunflower oil, castor oil, and coconut oil, a fatty acid such as palmitic acid, stearic acid, and linoleic acid, an organic acid such as acetic acid or a combination thereof. The culturing may be performed by using glucose as a carbon source. The nitrogen source may include an organic nitrogen source such as peptone, yeast extract, meat extract, malt extract, corn steep liquid, and soybean, an inorganic nitrogen source such as urea, ammonium sulfate, ammonium chloride, ammonium phosphate, ammonium carbonate, and ammonium nitrate or a combination thereof. The culture medium may include as a phosphorous source, for example, potassium dihydrogen phosphate, dipotassium phosphate, a sodium-containing salt corresponding to potassium dihydrogen phosphate, and dipotassium phosphate, and a metal salt such as magnesium sulfate and iron sulfate. In addition, an amino acid, a vitamin, and an appropriate precursor may be included in the culture medium. The culture medium or an individual component may be added to the culture solution in a batch mode or a continuous mode.

In addition, pH of the culture solution may be adjusted during the culturing by adding a compound such as ammonium hydroxide, potassium hydroxide, ammonia, phosphoric acid and sulfuric acid to the culture in an appropriate mode. In addition, bubble formation may be repressed by using an anti-foaming agent such as fatty acid polyglycol ester.

The oxygen conditions of culturing the microorganism may be aerobic conditions having a normal oxygen partial pressure or anaerobic conditions.

The term "anaerobic conditions" herein refers to a state wherein oxygen content is lower than that of normal atmospheric state. The anaerobic conditions may represent a state wherein oxygen content of the air at a site where culturing is performed is lower than 21%. In addition, oxygen content under anaerobic conditions may be 20% or lower, 15% or lower, 10% or lower, 5% or lower, or 1% or lower of the oxygen content of the atmosphere. In addition, dissolved oxygen in culture medium under anaerobic conditions may be lower than the dissolved oxygen of normal atmosphere. The dissolved oxygen under anaerobic conditions may be 10 ppm or lower, 8 ppm or lower, 5 ppm or lower, 3 ppm or lower, or 2 ppm or lower. Or, the dissolved oxygen may be from about 0.1 ppm to about 1 ppm. Anaerobic conditions may be formed, for example, by supplying carbon dioxide or nitrogen at a flow rate range from about 0.1 vvm (Volume per Volume per Minute) to about 0.4 vvm, from about 0.2 vvm to about 0.3 vvm or at a flow rate of 0.25 vvm. In addition, anaerobic conditions may be formed by setting an aeration rate in the range from about 0 vvm and to 0.4 vvm, from about 0.1 vvm to about 0.3 vvm or from 0.15 vvm to about 0.25 vvm.

The recovering (or collecting) an organic acid from the culture solution may be performed by using a separation and purification method known in the art. The collecting of the organic acid may be performed by centrifugation, ion-exchange chromatography, filtration, precipitation, extraction, distillation, or combination thereof. For example, the culture solution may be centrifuged to separate biomass, and a supernatant thus obtained may be separated by ion-exchange chromatography.

Hereinafter, the present invention will be described in further detail with reference to examples. It will be obvious to a person having ordinary skill in the art that these examples are illustrative purposes only and are not to be construed to limit the scope of the present invention.

Example 1

Preparation of TBP Mutant Library

To induce a mutation at transcriptional machinery, genes related to a transcriptional machinery were selected. Among enzymes related to a transcriptional machinery, RNA polymerase II complex was selected. RNA polymerase II complex includes RNAP II, TFIID, TFIIB, TFIIF, TFIIE, TFIIH, TBP, TAF, and others. Among them, a TBP (TATA binding protein) gene was selected.

To induce various gene mutations throughout the entire TBP gene uniformly, the TBP gene (702 bp) were divided into four domains, each of which has about 175 bp, and a mutation was induced in each domain by ep-PCR. The resulting domains were connected again by ep-PCR to complete the final TBP mutant library (including more than $10^3$ gene fragments) (FIG. 1). A fragment mutagenesis was performed with the four domains (D1 to D4), each of which has 175 bp of the entire TBP gene, by using the following four pairs of primers, a genomic DNA of *Kluyveromyces marxianus* as a template, and a Genemorphll Random Mutagenesis kit (Stratagene).

TABLE 1

Primer sets to perform TBP gene mutation

| Name | Sequence | SEQ ID NO. |
|---|---|---|
| TBP D1 F XbaI | 5'-GCTCTAGA ATGTCTGAAGA TGATAGAAT-3' | SEQ ID NO: 7 |
| TBP D1 R | 5'-TAGGTATGATTCCCGATGT A-3' | SEQ ID NO: 8 |
| TBP D2 F | 5'-TACATCGGGAATCATACCTA CTCTACAGAATATTGTTGCG-3' | SEQ ID NO: 9 |
| TBP D2 R | 5'-GTAACAACCATCTTACCAG' A-3 | SEQ ID NO: 10 |
| TBP D3 F | 5'-TCTGGTAAGATGGTTGTTAC GGGTGCTAAAAGTGAAGATG-3' | SEQ ID NO: 11 |
| TBP D3 R | 5'-GAAAGTACCGTGACTAAAT G-3' | SEQ ID NO: 12 |
| TBP D4 F | 5'-CATTTAGTCACGGTACTTTC TCGTCATATGAACCAGAACT-3' | SEQ ID NO: 13 |
| TBP D4 R SmaI | 5'-TCCCCCGGG TCATTATAAT TTTCTGAATT-3' | SEQ ID NO: 14 |

According to the protocol of the kit, fragments mutated at a low frequency (0 to 4.5 mutations/kb), fragments mutated at a medium frequency (4.5 to 9 mutations/kb), and fragments mutated at a high frequency (9-16 mutations/kb) were obtained.

A fragment mutagenesis was performed by using the fragments D1 and D2 as templates, TBP D1 F Xbal and TBP D2 R primers, and Genemorphll Random Mutagenesis kit (Stratagene) to obtain a secondary mutation fragment (D1/2) in which D1 and D2 are connected to form one domain. In addition, a fragment mutagenesis was performed by the same method by using the fragments D3 and D4 as templates and TBP D3 F and TBP D4 R Smal primers to obtain a secondary mutation fragment (D3/4) in which D3 and D4 were connected to form one domain. Lastly, a fragment mutagenesis was performed by the same method by using the fragments D1/2 and D3/4 as templates and D1 F Xbal and TBP D4 R Smal to obtain a tertiary mutation fragment of the entire TBP gene in which all the four domains were connected. The mutated TBP gene fragment obtained by the method was cleaved by using restriction enzymes Xbal and Smal and the resulting fragments were introduced to pJSKM316-GPD vector (Appl Microbiol Biotechnol. 2013 March; 97(5):2029-41. Characterization of *Saccharomyces cerevisiae* promoters for heterologous gene expression in *Kluyveromyces marxianus*) which was also cleaved by using Xbal and Smal to complete final TBP mutant library (including more than $10^3$ gene fragments).

The plasmid library was introduced into *E. coli* DH5α. Then, the transformed strain was spread on a LB-agar plate including 100 μg/ml ampicillin to culture the strain. The estimated size of the entire library was about $10^5$. The cultured *E. coli* colony was picked up from the plate and the plasmid was obtained by using plasmid MiniPrep Spin Kit. Then, the obtained plasmid was introduced into yeast.

The number of gene mutations in the TBP library prepared by the method was analyzed. The result showed that the number of gene mutations was about two times greater than that obtained by the known general method of inducing mutation by ep-PCR without dividing a gene into domains (Table 2).

TABLE 2

| TBP mutagenesis rate | | |
|---|---|---|
| TBP mutagenesis rate | Known Method | Mutagenesis in Divided Domains (One Embodiment) |
| High (16 bp/kb) | 10~22 bp | 11 bp |
| Low (9 bp/kb) | 24 bp | 4.2 bp |

Example 2

Development of an Improved Acid-Resistant *Kluyveromyces marxianus* Using TBP Mutant Library To verify an introduction of acid-resistance to a wild type *Kluyveromyces marxianus* by an introduction of a wild type TBP gene which was not mutated, a plasmid including a wild type TBP gene was prepared and introduced to a *Kluyveromyces marxianus* strain. In order to obtain a plasmid including a wild type TBP gene, a PCR was performed by using *Kluyveromyces marxianus* genomic DNA as a template, and primers TBP D1 F Xbal and TBP D4 R Smal, and the resulting gene fragments were obtained. The obtained wild type TBP gene fragments were cleaved by using restriction enzymes Xbal and Smal and then the resulting fragments were introduced to the pJSKM316-GPD vector which was also cleaved by using Xbal and Smal. The plasmid including the prepared wild type TBP gene was introduced to the *Kluyveromyces marxianus* strain and the survival and growth of the strain was verified at pH 7, which is a normal growth condition, and at pH 2.5, which is a growth condition under which a *Kluyveromyces marxianus* is unable to grow.

In the case of the wild type *Kluyveromyces marxianus* strain to which a TBP gene in which no mutation was induced was introduced, the *Kluyveromyces marxianus* strain normally survived and grew at pH 7. However, the *Kluyveromyces marxianus* strain formed almost no colony and was unable to survive under pH 2.5 condition (Table 3). Therefore, the subsequent selection of acid-resistant *Kluyveromyces marxianus* strain using the TBP mutant library was performed at the condition of pH 2.5.

TABLE 3

| Acid-resistance of *Kluyveromyces marxianus* strain by wild type TBP gene | | |
|---|---|---|
| | pH 7 | pH 2.5 |
| Number of Colonies | 207 | 7 |

The TBP mutant library prepared by the method of Example 1 was introduced to *Kluyveromyces marxianus* strain and the *Kluyveromyces marxianus* strain which was capable of surviving and growing under the condition of pH 2.5, which was a condition under which a *Kluyveromyces marxianus* strain to which a plasmid including a wild type TBP gene was introduced was unable to survive, was selected (Table 4).

TABLE 4

| Acid-resistance of *Kluyveromyces marxianus* strain by TBP mutant library (number of colonies formed) | | |
|---|---|---|
| | Wild Type TBP | TBP mutant Library |
| pH 5.4 | 201 | 365 |
| pH 2.5 | 0 | 257 |

As described above, it was verified that both *Kluyveromyces marxianus* strain prepared by using the TBP mutant library and the *Kluyveromyces marxianus* strain including the wild type TBP grew well at pH 5.4. At pH 2.5, the *Kluyveromyces marxianus* strain including the wild type TBP did not form a colony, but the *Kluyveromyces marxianus* strain having the mutated TBP gene grew well and formed many colonies as under the condition of pH 5.4. The transformed *Kluyveromyces marxianus* strain which well survived and grew even under the low pH condition was selected and the TBP mutation site of the strain was verified by DNA sequencing (SEQ ID NOS: 2 to 4).

TBP15 (wild-type amino acids sequence):<br>
SEQ ID NO: 1<br>
MSEDDRMKQFQQENKIVFDPSTRSVWESQEKREHESLPGTDANGDEGEKG<br>
SATSGIIPTLQNIVATVNLDCRLDLKTVALHARNAEYNPKRFAAVIMRIR<br>
EPKTTALIFASGKMVVTGAKSEDDSKLASRKYARIIQKIGFSAKFTDFKI<br>
QNIVGSCDVKFPIRLEGLAFSHGTFSSYEPELFPGLIYRMVKPKIVLLIF<br>
VSGKIVLTGAKQREEIYQAFEAIYPVLSEFRKL TBP15-M1 (Mutated amino acids sequence):<br>
SEQ ID NO: 2<br>
MSEDDRMKQFLQENKIVFDPSTRSVWGSQEKREHESLQGTDANADEGEKG<br>
SATSGIIPTLQNIVATVNLDCRLDLKTVALHARNAEYNPERFAAVIMRIR<br>
EPKTTALIFASGKMVVTGAKSEDDSKLASRKYARIIQKIGFSAKFTDFKI<br>
QNIVGSCDVKFPIRLEGLAFSHGTFSSYEPELFPGLIYRMVKPKIVLLIF<br>
VSGKTVLTGAKQREEIHQAFEAIYPVLSEFRKL TBP15-M2 (Mutated amino acids sequence):<br>
SEQ ID NO: 3:<br>
MSEDDRMKQFQQENKIVFDPSTRSVWEGQERREHESLPGTDANADEGEKG<br>
SATSGIIPTLQNIVATVNLDCRLDLKTVALHARNSEYNPKRFAAVIMRIS<br>
EPKTTALIFASGKMVVTGAKSEDDSKLACRKYARIIQKIGFSAKFTDFKI<br>
QDIVGSCDVKFPIRLEGLAFSHGTFSSCEPELFPGLIYRMVKPKIVLLIF<br>
DSGKIVLTGAKQREEIYQAFEAIYPVLSEFRKL TBP15-M3 (Mutated amino acids sequence):<br>
SEQ ID NO: 4:<br>
MSEDDRMKQFQQENKIVFDPSTRSVWESQEKREHESLPGTDANADEGEKG<br>
SATSGIIPTLQNIVATVNLDCRLDLKTVALHARNAEYNPKRFAAVVMRIR<br>
EPKTTALIFASGKMVVTGAKSEDDSELASRKYARIIQKIGFSAKFTDFKI<br>
QNIVGSCDVKFPIRLEGLAFSHGTFSSYEPELIPGLIYRMVKPKIVLLIF<br>
VSGKIVLTEAKQREEIYQAFEAIYPVLCEFRKL

Example 3

Preparation of 3-HP Producing Strain by Introduction of Enzymes and Verification of 3-HP Production The *Kluyveromyces marxianus* strain including the sequences of SEQ ID NO: 2 to 4 was selected. To verify the effect of the enzymes on 3-HP production by using the selected strain, polynucleotides encoding enzymes to produce 3-HP were introduced to the strain. The enzymes to produce 3-HP were malonyl coA reductase (EC 1.2.1.75) catalyzing a reaction of converting malonyl-coA and malonic semialdehyde and malonate semialdehyde reductase (EC 1.1.1.298) catalyzing a reaction of converting malonic semialdehyde to 3-HP. The malonyl coA reductase is an enzyme having an amino sequence of SEQ ID NO: 5 and malonate semialdehyde reductase is an enzyme having an amino sequence of SEQ ID NO: 6. The polynucleotides encoding the proteins were introduced to the strain through a vector. To express the proteins, the polynucleotides encoding the proteins were introduced to pKDU7 vector for an expression in the *Kluyveromyces marxianus* strain (Danguole Bartkeviciute et al., Enzyme and Microbial Technology 26, 2000, 653-656). It was verified that the strain produced by the method continuously produced 3-HP under the condition of pH 4.0 or lower in comparison with a strain prepared by introducing malonyl coA reductase and malonate semialdehyde reductase to a strain to which a wild type TBP was introduced.

As described above, according to the one or more of the above embodiments of the present invention, to use *Kluyveromyces marxianus* as a host strain useful for various industrial purposes, gene expression in *Kluyveromyces marxianus* was comprehensively reconstructed and, as a result, a transformed strain in which cellular functions were improved and new functions were provided was developed. In particular, through the strain, a *Kluyveromyces marxianus* strain having high acid-resistance was developed. The *Kluyveromyces marxianus* strain was routinely maintained on standard yeast media (YPD) at 30° C. The developed strain may be used in industry as an optimized strain for producing 3-HP, which is an industrial platform compound, and other various useful organic acid at a high concentration.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A recombinant *Kluyveromyces marxianus* yeast cell comprising a gene encoding a mutated subunit of the RNA polymerase II (RNAP II) complex, wherein the mutated subunit increases the acid resistance of the yeast cell, and the mutated subunit is a mutated TATA-box binding protein (TBP) comprising a sequence selected from the group consisting of SEQ ID NO: 2, 3, and 4.

2. The recombinant *Kluyveromyces marxianus* yeast cell of claim 1, wherein the *Kluyveromyces marxianus* yeast cell is capable of surviving or growing at a pH of 2.5 or lower.

3. The recombinant *Kluyveromyces marxianus* yeast cell of claim 1, wherein the *Kluyveromyces marxianus* yeast cell further comprises a heterologous polynucleotide encoding a protein needed to synthesize an organic acid or 1,4-butandiol, and the organic acid is lactic acid, succinic acid, malic acid, 3-hydroxypropionic acid or 4-hydroxybutyric acid.

4. The recombinant *Kluyveromyces marxianus* yeast cell of claim 1, wherein the *Kluyveromyces marxianus* yeast cell comprises at least one pathway selected from the group consisting of malonyl CoA pathway, β-alanine pathway, and glycerol pathway.

5. The recombinant *Kluyveromyces marxianus* yeast cell of claim 3, wherein the heterologous polynucleotide encodes a protein selected from the group consisting of 3-hydroxyisobutyl-CoA hydrolase, 3-hydroxyisobutyrate dehydrogenase, 3-hydroxypropionyl-CoA hydrolase, 3-hydroxypropionyl-CoA dehydratase, acetyl-CoA carboxylase, aspartate decarboxylase, CoA transferase, malonyl-CoA reductase, phosphoenolpyruvate (PEP) carboxylase, 3-oxopropanoate: NADP+ oxidoreductase, malonate semialdehyde reductase, 3-hydroxypropionate dehydrogenase, 4-aminobutyrate aminotransferase, acetyl-CoA carboxylase, aspartate aminotransferase, aspartate decarboxylase, glutamate dehydrogenase, OS17 enzyme, pyruvate carboxylase, β-alanyl-CoA ammonia lyase, glycerol dehydratase, and aldehyde dehydrogenase.

6. The recombinant *Kluyveromyces marxianus* yeast cell of claim 1, wherein the *Kluyveromyces marxianus* further comprises a heterologous polynucleotide encoding a protein selected from the group consisting of 3-hydroxyisobutryl-CoA hydrolase, 3-hydroxyisobutyrate dehydrogenase, 3-hydroxypropionyl-CoA hydrolase, 3-hydroxypropionyl-CoA dehydratase, acetyl-CoA carboxylase, aspartate decarboxylase, CoA transferase, malonyl-CoA reductase, PEP carboxylase, 3-oxopropanoate:NADP+ oxidoreductase, malonate semialdehyde reductase, and 3-hydroxypropionate dehydrogenase.

7. The recombinant *Kluyveromyces marxianus* yeast cell of claim 1, wherein the *Kluyveromyces marxianus* further comprises one or more heterologous polynucleotides encoding 3-oxopropanoate:NADP+ oxidoreductase and 3-hydroxypropionate dehydrogenase.

8. The recombinant *Kluyveromyces marxianus* yeast cell of claim 6, wherein the *Kluyveromyces marxianus* further comprises one or more heterologous polynucleotides encoding malonyl-CoA reductase and malonate semialdehyde reductase.

9. The recombinant *Kluyveromyces marxianus* yeast cell of claim 1, wherein the *Kluyveromyces marxianus* yeast cell further comprises a heterologous polynucleotide encoding a protein selected from the group consisting of 3-hydroxyisobutyrate dehydrogenase, 4-aminobutyrate aminotransferase, acetyl-CoA carboxylase, aspartate aminotransferase, aspartate decarboxylase, glutamate dehydrogenase, OS17 enzyme, pyruvate carboxylase, β-alanyl-CoA ammonia lyase, and 3-hydroxypropionate dehydrogenase.

10. The recombinant *Kluyveromyces marxianus* yeast cell of claim 1, wherein the *Kluyveromyces marxianus* yeast cell further comprises a heterologous polynucleotide encoding 3-hydroxypropionate dehydrogenase.

11. The recombinant *Kluyveromyces marxianus* yeast cell of claim 1, wherein the *Kluyveromyces marxianus* yeast cell further comprises one or more heterologous polynucleotides encoding glycerol dehydratase and aldehyde dehydrogenase.

12. A method of producing an organic acid comprising culturing a recombinant *Kluyveromyces marxianus* yeast cell of claim 1, whereby the yeast cell produces an organic acid; and recovering the organic acid from the culture solution.

13. The method of claim 12, wherein the organic acid is selected from the group consisting of 3-hydroxypropionate (3-HP), 1,4-butandiol, lactic acid, and succinic acid.

14. The method of claim 12, wherein the organic acid is a 3-hydroxypropionate (3-HP) and the heterologous polynucleotide encodes a protein selected from the group consisting of 3-hydroxyisobutryl-CoA hydrolase, 3-hydroxyisobutyrate dehydrogenase, 3-hydroxypropionyl-CoA hydrolase, 3-hydroxypropionyl-CoA dehydratase, acetyl-CoA carboxylase, aspartate decarboxylase, CoA transferase, malonyl-CoA reductase, PEP carboxylase, 3-oxopropanoate:NADP+ oxidoreductase, malonate semialdehyde reductase, and 3-hydroxypropionate dehydrogenase.

15. The method of claim 12, wherein the organic acid is a 3-hydroxypropionate (3-HP) and the heterologous polynucleotide encodes a protein selected from the group consisting of 3-hydroxyisobutyrate dehydrogenase, 4-aminobutyrate aminotransferase, acetyl-CoA carboxylase, aspartate aminotransferase, aspartate decarboxylase, glutamate dehydrogenase, OS17 enzyme, pyruvate carboxylase, β-alanyl-CoA ammonia lyase, and 3-hydroxypropionate dehydrogenase.

16. The method of claim 12, wherein the organic acid is a 3-hydroxypropionate (3-HP) and the *Kluyveromyces marxianus* yeast cell further comprises one or more heterologous polynucleotides encoding glycerol dehydratase and aldehyde dehydrogenase.

17. The method of claim 12, wherein the recombinant *Kluyveromyces marxianus* yeast cell is cultured under aerobic conditions.

* * * * *